United States Patent
Mullin et al.

[11] Patent Number: 5,504,261
[45] Date of Patent: Apr. 2, 1996

[54] PRODUCTION OF HYDROXY COMPOUNDS

[75] Inventors: Thomas C. Mullin, Exton; Nicholas Triantafillou, West Chester, all of Pa.

[73] Assignee: ARCO Chemical Technology, L.P., Greenville, Del.

[21] Appl. No.: 283,887

[22] Filed: Aug. 1, 1994

[51] Int. Cl.$^6$ .................................................. C07C 27/04
[52] U.S. Cl. ..................... 568/862; 568/882; 568/454
[58] Field of Search ..................... 568/454, 862, 568/882

[56] References Cited

U.S. PATENT DOCUMENTS

| | | |
|---|---|---|
| 4,083,882 | 4/1978 | Taylor et al. .......................... 568/862 |
| 4,215,077 | 7/1980 | Matsumoto et al. . |
| 4,238,419 | 12/1980 | Matsumoto et al. . |
| 4,317,936 | 3/1982 | Kim et al. .............................. 568/882 |
| 4,678,857 | 7/1987 | Dureanleau et al. . |
| 5,166,370 | 11/1992 | Liotta et al. ........................... 568/862 |
| 5,290,743 | 3/1994 | Chang . |

FOREIGN PATENT DOCUMENTS 8349532  7/1979  Japan .

Primary Examiner—Rebecca Cook
Attorney, Agent, or Firm—William C. Long

[57] ABSTRACT

A process for producing a hydroxy compounds such as butanol or butanediol by hydroformylation of an olefin using a precious metal and phosphorus compound catalyst system, water extraction of the aldehyde product and hydrogenation of the extracted aldehyde where the aqueous extract is treated with an ion exchange resin before hydrogenation to increase hydrogenation catalyst life.

4 Claims, No Drawings

PRODUCTION OF HYDROXY COMPOUNDS

BACKGROUND OF THE INVENTION

1. Field of the Invention

The present invention relates to an improved process for the production of hydroxy compounds by the catalytic hydrogenation of aldehydes such as n-butyraldehyde or n-hydroxybutyraldehyde which result from hydroformylation using a precious metal and phosphorus compound catalyst system. The invention is especially concerned with prolonging the life of the hydrogenation catalyst by treating the aqueous aldehyde hydroformylation stream with an ion exchange resin prior to hydrogenation.

2. Description of the Prior Art

The hydroformylation of olefinic compounds in the presence of precious metal and phosphorus compound catalyst systems is well known. The process is used commercially to manufacture n-butyraldehyde from propylene and n-hydroxybutyraldehyde (4hydroxybutanol) from allyl alcohol. See, for example, U.S. Pat. Nos. 4,238,419, 4,678,857, 4,215,077, 5,290,743 and the like.

In general, the hydroformylation reaction product mixture, which is usually in an organic solvent such as toluene, is contacted with an aqueous extraction stream which extracts the hydroformylation products from an organic phase which contains the catalyst materials. The organic phase can be recycled to the hydroformylation while the aqueous phase is subjected to hydrogenation to convert the contained aldehydes to hydroxy compounds such as n-butanol and 1,4-butanediol. See, for example, Japanese Patent Publication No. 49532/83.

A problem which has existed in this technology has been the tendency for the hydrogenation catalyst, used to convert the aldehydes to hydroxy compounds, to deactivate with time. It is an object of the present invention to provide a process whereby the life of the hydrogenation catalyst can be substantially extended.

BRIEF DESCRIPTION OF THE INVENTION

In accordance with the present invention it has been found that hydrogenation catalyst life can be significantly extended if the aqueous aldehyde extract stream from the hydroformylation is contacted with an ion exchange resin prior to the hydrogenation.

DETAILED DESCRIPTION

The process of the present invention is applicable to the aqueous aldehyde extract streams which are obtained by known hydroformylation and aqueous extraction procedures as illustrated, for example, in U.S. Pat. Nos. 4,215,077, 4,238,419, 5,290,743, and the like. As is well known, propylene, allyl alcohol and the like can be hydroformylated in an organic solvent in the presence of a rhodium complex and a trisubstituted phosphine to give a reaction mixture comprising butyraldehyde, hydroxybutyraldehyde, and the like and these products can be separated from the organic solvent and the rhodium and phosphine catalyst system by aqueous extraction. It is the aqueous extract streams prepared in accordance with known procedures which are treated by the process of this invention.

In accordance with the invention, the said aqueous extract stream is contacted with ion exchange resin. The contact is suitably carried out by passing the liquid aqueous extract stream through a bed of the ion exchange resin at temperatures ranging from 0° to 120° C., preferably 10° to 40° C.

Both anion and cation exchange resins can be used in practice of the invention. Ion exchange resins which are employed in practice of the invention include basic anion exchange resin which are well known articles of commerce. Both strong-base resins and weak-base resins can be used.

Strong-base resins can be produced by the reaction between chlormethylated styrene-DVB copolymer and a tertiary amine such as trimethyl amine, which results in a resin with quaternary ammonium groups.

The principal types of weak-base anion exchangers are amine derivatives of styrene-DVB copolymers, epichlorohydrin-amine condensation products, and amine derivatives of phenol-formaldehyde products, and may contain primary, secondary or tertiary amine groups, or mixtures of some or all of these groups.

Weak-base styrene-DVB resins can be made, for example, by aminating chloromethylated copolymer in much the same way the strong-base styrene-DVB resins are made, except that primary or secondary amines are generally used instead of a tertiary amine.

U.S. patent numbers which describe the preparation of basic anion resins useful in the present invention include: 4,025,467, 3,791,996, 3,817,878, 3,346,516, 4,082,701, 3,843,566, 3,813,353, 3,812,061, 3,882,053, 3,793,273, 3,296,233, 3,108,922, 3,005,786, 3,637,535, and 4,052,343.

Cation exchange resins can be employed but since strongly acidic materials tend to promote undesirable side reactions in the system, the cation resins should first be treated to replace the proton with alkali metal or ammonium before use. Sulfonic acid cationic exchange resins such as Amberlyst 15 and Amberlite IR-120 where the proton is replaced by Na, K or $NH_4$ are advantageously employed.

Thereafter, the aqueous extract stream is separated from the resin bed and subjected to hydrogenation using a nickel catalyst, e.g. Raney nickel, in accordance with known procedures to form the hydroxy compound product, ie. n-butanol from butyraldehyde and 1,4 butanediol from n-hydroxybutyraldehyde.

While not intending to be bound by theory, it is believed that the ion exchange resin treatment removes phosphorus compounds from the aqueous extract which originate with the hydroformylation catalyst system and which are poisons as far as activity of the nickel hydrogenation catalyst is concerned. Whatever the theory, the effect of the ion exchange resin treatment is to substantially extend the life of the nickel hydrogenation catalyst in the butanediol production step.

The invention can best be illustrated by the following examples.

In each case, allyl alcohol was hydroformylated in accordance with the procedure set forth in U.S. Pat. No. 5,290,743 using the rhodium triphenyl phosphine and 1,4-bis(diphenylphosphino)butane catalyst system described therein using a synthesis gas having a $CO:H_2$ ratio of about 1:4 at a temperature of about 65° C., a pressure of about 2 kg/cm², in a toluene solvent. The reactor effluent from the hydroformylation was chilled and the product n-hydroxybutyraldehyde was water extracted from the catalyst and organic solvent.

The aqueous extract stream was passed through a bed of the Na form of Amberlite IR-120 at a LHSV of 8 $hr^{-1}$ and then hydrogenated. The hydrogenation was carried out in an agitated 300 ml autoclave reactor with 6 g of Raney nickel catalyst slurried therein. Aqueous extract feed rate was 175 ml/hr, residence time in the reactor was 1.5 hours. The hydrogen feed rate was 28 SLH, hydrogenation temperature was 100° C. or 110° C. and reactor agitation rate was 800 RPM.

Catalyst activity was measured in terms of the formation of the ether condensation product 2-(4)-hydroxy butoxy tetrahydrofuran; with an active hydrogenation catalyst essentially none of this condensation product is formed.

Reactor runs were continued until the concentration of the condensation product designated in the table as X-13, reached about 0.1% as a measure of hydrogenation catalyst active life. The following table shows the results achieved in comparison to comparable runs where the resin treatment of the invention was not employed.

TABLE 1

| Run | Resin Treatment | Run Time hr | Temp. °C. | Residual X-13 wt % |
|---|---|---|---|---|
| 1 | Yes | 432 | 100 | 0.14 |
| A | No | 80 | 100 | 0.13 |
| B | No | 79 | 100 | 0.10 |
| 2 | Yes | >297 | 100 | 0.04 |
| 3 | Yes | >197 | 100 | 0.01 |
| 4 | Yes | 126 | 110 | 0.5 |
| 5 | Yes | 149 | 110 | 0.2 |
| C | No | 50 | 110 | 0.1 |

The above data show that catalyst life as measured by formation of the condensation ether was greatly extended by the ion exchange resin treatment of the invention.

I claim:

1. In a process wherein an olefin is hydroformylated in an organic solvent in contact with a catalyst system comprised of rhodium and phosphine to form a reaction product comprised of aldehyde, the hydroformylation reaction mixture is contacted with water and an aldehyde containing aqueous stream is phase separated from organic solvent and catalyst, and the aldehyde containing aqueous stream is hydrogenated in contact with a nickel hydrogenation catalyst, the improvement which comprises contacting the separated aldehyde containing aqueous stream before hydrogenation with an ion exchange resin at 0° C. to 120° C., separating the aqueous aldehyde containing stream from the ion exchange resin and hydrogenating the separated ion exchange resin treated aqueous aldehyde containing stream using a nickel hydrogenation catalyst to convert contained aldehyde to the corresponding hydroxy compound.

2. The process of claim 1 wherein n-butanol is prepared from propylene.

3. The process of claim 1 wherein 1,4-butanediol is prepared from allyl alcohol.

4. The process of claim 1 wherein the hydrogenation catalyst is a Raney nickel catalyst.

* * * * *